United States Patent
Su et al.

(10) Patent No.: US 8,501,166 B2
(45) Date of Patent: Aug. 6, 2013

(54) PYRIMIDINYL INDOLE COMPOUNDS

(75) Inventors: Wei-Guo Su, Shanghai (CN); Jinshui Li, Shanghai (CN)

(73) Assignee: Hutchison Medipharma Limited, Shanghai (CN)

( * ) Notice: Subject to any disclaimer, the term of this patent is extended or adjusted under 35 U.S.C. 154(b) by 0 days.

(21) Appl. No.: 13/643,291

(22) PCT Filed: Apr. 27, 2010

(86) PCT No.: PCT/CN2010/072225
§ 371 (c)(1),
(2), (4) Date: Nov. 20, 2012

(87) PCT Pub. No.: WO2011/134140
PCT Pub. Date: Nov. 3, 2011

(65) Prior Publication Data
US 2013/0058892 A1    Mar. 7, 2013

(51) Int. Cl.
| | |
|---|---|
| A61K 31/506 | (2006.01) |
| A61K 38/19 | (2006.01) |
| A61P 35/00 | (2006.01) |
| A61P 19/02 | (2006.01) |
| A61P 11/06 | (2006.01) |
| A61P 1/00 | (2006.01) |
| A61P 29/00 | (2006.01) |
| C07D 403/04 | (2006.01) |

(52) U.S. Cl.
USPC .......................................................... 424/85.1

(58) Field of Classification Search
USPC .......................................................... 424/85.1
See application file for complete search history.

(56) References Cited

U.S. PATENT DOCUMENTS

2007/0244139 A1    10/2007    Ritzeler et al.

FOREIGN PATENT DOCUMENTS

| WO | WO-2004/022553 A1 | 3/2004 |
| WO | WO-2004/089913 A1 | 10/2004 |
| WO | WO-2005/113544 A1 | 12/2005 |
| WO | WO-2006/038001 A1 | 4/2006 |
| WO | WO-2006/075152 A1 | 7/2006 |
| WO | WO-2006/076318 A1 | 7/2006 |
| WO | WO-2007/092095 A2 | 8/2007 |

*Primary Examiner* — Jeffrey S. Lundgren
*Assistant Examiner* — Zenab Olabowale
(74) *Attorney, Agent, or Firm* — Birch, Stewart, Kolasch & Birch, LLP.

(57) ABSTRACT

The present invention provides pyrimidinyl indole compounds as novel kinase inhibitors for the treatment of cancer and inflammatory diseases.

34 Claims, No Drawings

PYRIMIDINYL INDOLE COMPOUNDS

This application is the National Stage Under 35 U.S.C. §371 of PCT International Application No, PCT/CN2010/072225 filed on Apr.27, 2010. The entire contents of which are hereby incorporated by reference.

This invention is directed to pyrimidinyl indole compounds, formulations, and therapeutic uses thereof, particularly in the treatment of cancer and inflammatory diseases.

IKKβ is a key kinase regulating inflammation and stress related pathways and thus has been linked to the development of a variety of human diseases ranging from cancer to inflammatory diseases.

Pyrimidinyl indole compounds useful as kinase inhibitors are already known in the art. See WO04089913 (IKKβ inhibitors), WO06038001, and WO06075152.

Additionally, pyrimidinyl benzothiophene compounds useful as inhibitors of IKKβ are also known in the art. See WO07092095.

There is a need for potent IKKβ inhibitors useful for treatment of cancer or inflammatory diseases. There is also a need for such compounds that have a synergistic affect when combined with TNFα or vincristine (VCR).

The present invention provides novel pyrimidinyl indole compounds with clinical use for treatment of cancer and inflammatory diseases through inhibiting IKKβ. More specifically, the present invention provides novel pyrimidinyl indole compounds of the formula:

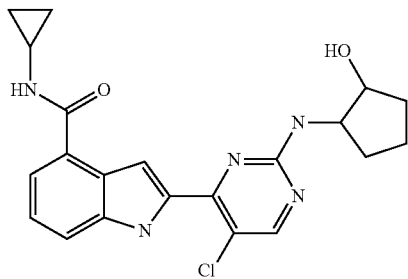 [SMILES: O=C(NC1CC1)c1cccc2[nH]c(-c3nc(NC4CCCC4O)ncc3Cl)cc12]

or a pharmaceutically acceptable salt thereof.

The present invention also provides a method of treating cancer selected from the group consisting of multiple myeloma, colon cancer, large cell lung cancer, glioblastoma, pancreatic cancer, and ovarian cancer in a mammal comprising administering to a mammal in need of such treatment an effective amount of a compound or salt of the present invention.

The present invention also provides a method of treating inflammatory diseases selected from the group consisting of rheumatoid arthritis, chronic obstructive pulmonary disease, asthma, multiple sclerosis, and inflammatory bowel disease, in a mammal comprising administering to a mammal in need of such treatment an effective amount of a compound or salt of the present invention.

The present invention also provides pharmaceutical compositions comprising a compound or salt of the present invention in combination with one or more pharmaceutically acceptable carriers, diluents, or excipients. In a particular embodiment the composition further comprises one or more other therapeutic agents. In a further embodiment the other therapeutic agent is TNFα. In a further embodiment the other therapeutic agent is vincristine.

The present invention also provides a compound or salt of the present invention for use in therapy. The present invention also provides a compound or salt of the present invention for use in the treatment of cancer. Additionally, the present invention provides use of a compound or salt of the present invention in the manufacture of a medicament for treating cancer. In particular these cancers are selected from the group consisting of multiple myeloma, colon cancer, large cell lung cancer, glioblastoma, pancreatic cancer, and ovarian cancer. One embodiment is multiple myeloma. Another embodiment is colon cancer. Another embodiment is large cell lung cancer. Another embodiment is glioblastoma. Another embodiment is pancreatic cancer. Another embodiment is ovarian cancer. The present invention also provides a compound or salt of the present invention for use in the treatment of inflammatory diseases. Additionally, the present invention provides use of a compound or salt of the present invention in the manufacture of a medicament for treating inflammatory diseases. In particular the inflammatory disease is selected from the group consisting of rheumatoid arthritis, chronic obstructive pulmonary disease, asthma, multiple sclerosis, and inflammatory bowel disease. One embodiment is rheumatoid arthritis. Another embodiment is chronic obstructive pulmonary disease. Another embodiment is asthma. Another embodiment is multiple sclerosis. Another embodiment is inflammatory bowel disease. Furthermore, the present invention provides a pharmaceutical composition for treating cancer selected from the group consisting of multiple myeloma, colon cancer, large cell lung cancer, glioblastoma, pancreatic cancer, and ovarian cancer comprising a compound or salt of the present invention as an active ingredient. Additionally, the present invention provides a pharmaceutical composition for treating inflammatory diseases selected from the group consisting of rheumatoid arthritis, chronic obstructive pulmonary disease, asthma, multiple sclerosis, and inflammatory bowel disease comprising a compound or salt of the present invention as an active ingredient.

Compounds and salts of the present invention are prepared essentially as illustrated in both the schemes and the examples. Further, all compounds and salts of the present invention exist as diastereomers or enantiomers due to cyclopentyl ring substitutions. Thus, optical purity is introduced by using specific diastereomers as reactants. Optical purity can also be introduced by using chromatography/chiral chromatography on mixtures of diastereomers or racemates corresponding to compounds or salts of the present invention.

Scheme I
Synthesis of Compounds of the Present Invention

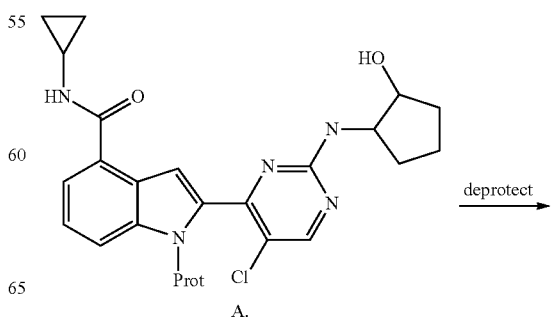

A.

-continued

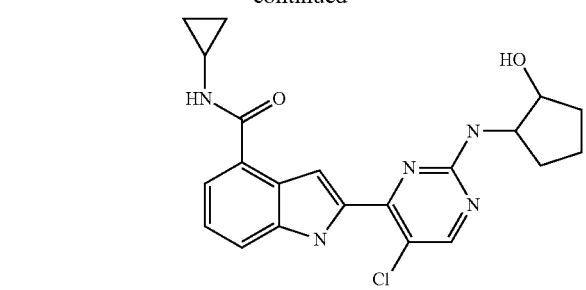

Prot = ethoxymethyl or tert-butoxycarbonyl

Compounds of the present invention are prepared by deprotection of their protected precursors (A) by treatment with HCl, trifluoroacetic acid (TFA) or p-toluenesulfonic acid (TsOH) in methanol or ethanol.

Scheme II
Synthesis of Precursors (A)

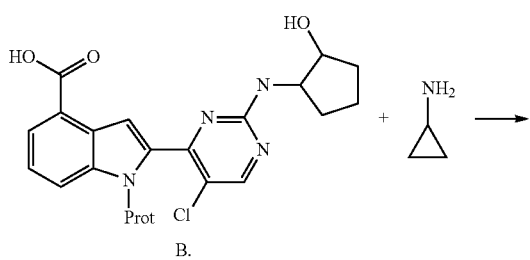

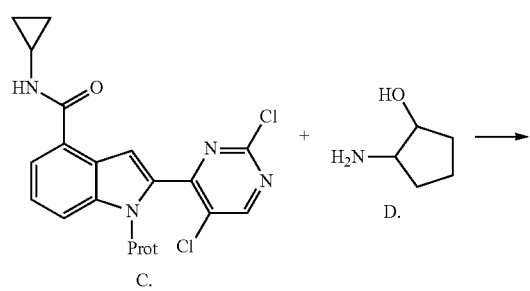

Precursors A are prepared in two ways illustrated above. In the upper reaction, an indole-4-carboxylic acid (B) is coupled with cyclopropylamine in the presence of a dehydrating agent, such as, benzotriazol-1-yloxytris(dimethylamino)-phosphonium hexafluorophosphate (BOP) or dicyclohexyl carbodiimide. One skilled in the art of organic synthesis will recognize that these amide coupling reactions may also take place at any convenient point in the synthetic sequences leading to compounds of Formula (I).

In the lower reaction, a 2-aminocyclopentanol (D), displaces the chloro group in the chloropyrimidine intermediate (C) in the presence of a base, such as, sodium hydride, diisopropylethyl amine (DIPEA) or potassium carbonate at elevated temperatures (70-130° C.) in solvents, such as, dimethyl sulfoxide (DMSO) or dimethyformamide (DMF). One skilled in the art of organic synthesis will recognize that these chloro displacement reactions may also take place at any convenient point in the synthetic sequences leading to compounds of the present invention.

Scheme III
Synthesis of carboxylic acid (B)

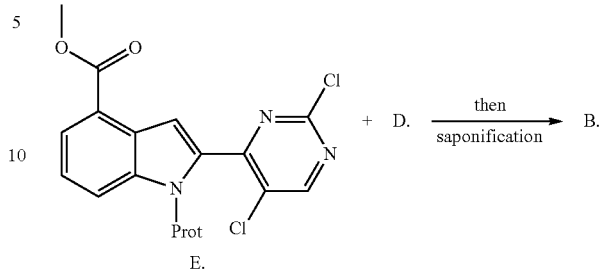

Indole-4-carboxylic acids (B) are prepared by displacement of the chloro group in pyrimidinyl ester (E) with a 2-aminocyclopentanol (D) similar to the lower reaction of Scheme II followed by saponification of the intermediate carboxylic acid ester group.

Scheme IV
Synthesis of pyrimidinyl chlorides (C) and (E)

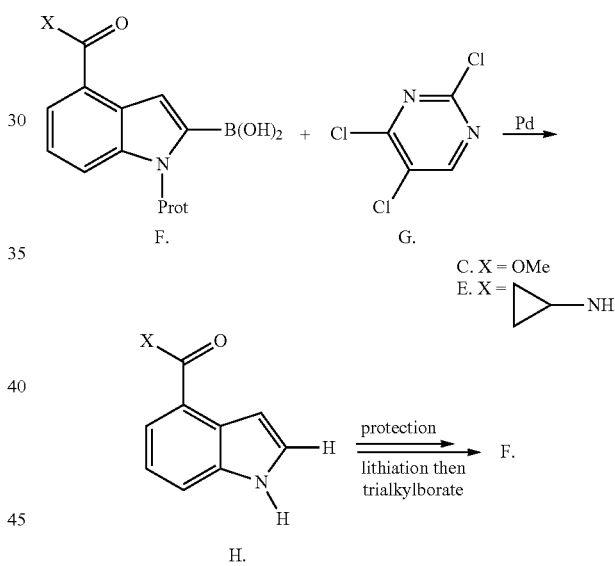

The pyrimidinyl chlorides (C) and (E) are prepared by palladium catalyzed coupling reactions of indole-2-boronic acids (F or their $C_1$-$C_3$ alkyl boronic esters) and the commercially available trichloropyrimidines (G). The catalyst is either $Pd(OAc)_2$, $Pd(PPh_3)_4$, or $PdCl_2(dppf)$, and the coupling reactions occur at elevated temperature (50-110° C.) in polar aprotic solvent, e.g., tetrahydrofuran (THF).

The indole precursors (H), which are either commercially available or prepared by literature methods, are first N1-protected in the presence of base with chloromethyl ethyl ether, $C_1$-$C_3$ trialkylsilyl chlorides, or di-tert-butyl dicarbonate followed by lithiation at the indole 2-position and treatment with $C_1$-$C_3$ trialkyl boronic esters to produce boronic acids or boronates (F).

The invention includes various stereoisomers and mixtures thereof. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution by methods well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

ChemDraw Ultra 10.0 is used to name the following compounds:

PREPARATION 1

N-Cyclopropyl-2-(2,5-dichloropyrimidin-4-yl)-1-(ethoxymethyl)-1H-indole-4-carboxamide (A) Preparation of methyl 1-(ethoxymethyl)-1H-indole-4-carboxylate Under nitrogen, to a solution of methyl 1H-indole-4-carboxylate (80 g, 0.46 mol) in THF (700 mL) is added potassium hexamethyldisilazide (1 M in THF, 550 mL, 0.55 mol) in drops at 0° C. The mixture is stirred at 0° C. for 30 minutes (min) and chloromethyl ethyl ether (51 mL, 0.55 mol) is then added at 0-5° C. After the addition, the reaction mixture is stirred at ambient temperature for another 3 hours (h), quenched carefully with 300 mL of water and extracted with ethyl acetate (EA, 3×300 mL). The combined extracts are washed with aqueous saturated sodium chloride (2×400 mL), then dried over $Na_2SO_4$, filtered and concentrated. The residue is purified by chromatography on silica gel to give the title compound (80 g, 75%). MS (m/z): 234 $(M+H)^+$.

(B) Preparation of 1-(ethoxymethyl)-1H-indole-4-carboxylic acid

To a solution of methyl 1-(ethoxymethyl)-1H-indole-4-carboxylate (135 g, 0.58 mol) in methanol (2 L) is added aqueous sodium hydroxide (68 g, 1.74 mol in 340 mL of $H_2O$). The reaction mixture is stirred at 50° C. for 3 h. The volatiles are removed in vacuo. The residue is acidified with HCl (2 M) until pH=3-4, then extracted with EA (2×700 mL). The combined extracts are washed with aqueous saturated sodium chloride (2×250 mL), dried over anhydrous $Na_2SO_4$, and concentrated to yield the title compound (123 g, 96%). MS (m/z): 220 $(M+H)^+$.

(C) Preparation of N-cyclopropyl-1-(ethoxymethyl)-1H-indole-4-carboxamide

To a solution of 1-(ethoxymethyl)-1H-indole-4-carboxylic acid (123 g, 0.56 mol) in THF (1.5 L) is added cyclopropylamine (58 mL, 0.84 mol) and triethylamine (TEA, 167 mL, 1.12 mol), followed by O-(7-azabenzotriazol-1-yl)-N,N,N',N'-tetramethyluronium hexafluorophosphate (240 g, 0.62 mol) at 0° C. The reaction mixture is stirred at ambient temperature overnight. The volatiles are removed in vacuo. The residue is stirred in EA (1.5 L) and HCl (0.5%, 1 L) for 10 minutes. The organic layer is separated, washed with aqueous saturated sodium chloride (3×100 mL), dried over anhydrous $Na_2SO_4$, filtered and concentrated. The residue is purified by chromatography on silica gel to give the title compound (110 g, 77%). MS (m/z): 259 $(M+H)^+$.

(D) Preparation of N-cyclopropyl-2-(2,5-dichloropyrimidin-4-yl)-1-(ethoxymethyl)-1H-indole-4-carboxamide To a solution of diisopropylamine (DIPA, 147 mL, 1.04 mol) in anhydrous THF (600 mL) is added n-BuLi (2.5 M in hexane, 420 mL, 1.04 mol) at −50 C. After the addition, the mixture is stirred at −20° C. for 30 minutes and then cooled to −70° C. A solution of N-cyclopropyl-1-(ethoxymethyl)-1H-indole-4-carboxamide (60 g, 0.23 mol) and tri(isopropyl) borate (56.4 mL, 0.25 mol) in anhydrous THF (300 mL) is added. The reaction mixture is stirred at −70° C. for 30 min. The reaction is slowly warmed up to ambient temperature, stirred for 1 h and then quenched with aqueous $K_3PO_4.3H_2O$ (195 g, 0.74 mol, in 700 mL of water). The crude reaction mixture is degassed and purged with $N_2$ for three times. 2,4,5-trichloropyrimidine (51 g, 0.27 mol) and palladium diphenylphosphinoferrocene dichloride ($PdCl_2(dppf).CH_2Cl_2$, 19.2 g, 0.023 mol) are added and stirred under nitrogen at refluxing temperature for 1.5 h. The volatiles are removed in vacuo. The residue is extracted with dichloromethane (DCM, 3×500 mL). The combined extracts are washed with aqueous saturated sodium chloride (3×100 mL), dried over anhydrous $Na_2SO_4$, filtered and concentrated. The residue is purified by chromatography on silica gel to give the title compound (30 g, 32%). MS (m/z): 405 $[(M+1)^+, {}^{35}Cl, {}^{35}Cl]$, 407 $[(M+1)^+, {}^{35}Cl, {}^{37}Cl]$ and 409 $[(M+1)^+, {}^{37}Cl, {}^{37}Cl]$.

EXAMPLE 1

2-{5-Chloro-2-[(1R,2S)-2-hydroxycyclopentylamino]pyrimidin-4-yl}-N-cyclopropyl-1H-indole-4-carboxamide hydrochloride

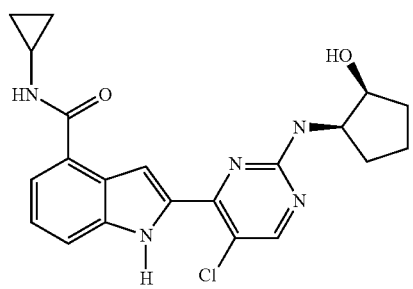 [SMILES: O=C(NC1CC1)c1cccc2[nH]c(-c3nc(N[C@@H]4CCC[C@@H]4O)ncc3Cl)cc12]

A mixture of N-cyclopropyl-2-(2,5-dichloropyrimidin-4-yl)-1-(ethoxymethyl)-1H-indole-4-carboxamide (10 g, 25 mmol), (1S,2R)-2-aminocyclopentanol hydrochloride (4.1 g, 30 mmol) and DIPEA (5 mL, 30 mmol) in DMSO (70 mL) is stirred at 100° C. for 3 h, then poured into water and extracted with EA. The combined extracts are washed with aqueous saturated sodium chloride, dried over $Na_2SO_4$ and concentrated in vacuo. The residue is purified by chromatography on silica gel to give 2-{5-chloro-2-[(1R,2S)-2-hydroxycyclopentylamino]pyrimidin-4-yl}-N-cyclopropyl-1-(ethoxymethyl)-1H-indole-4-carboxamide (7 g, 60.3%). MS (m/z): 470 $({}^{35}Cl)$ and 472 $({}^{37}Cl)$ $(M+H)^+$ The above product (7 g, 14 9 mmol) is stirred with hydrogen chloride (6 M in methanol, 210 mL, 1.26 mol) at 45° C. for 12 h. The precipitate is collected by filtration, washed with methanol and dried in vacuo to give the title compound (4.7 g, 70%). MS (m/z): 412 ($^{35}$Cl) and 414 ($^{37}$Cl) (M+H)$^+$.

EXAMPLE 2

2-{5-Chloro-2-[(1R,2R)-2-hydroxycyclopentylamino]pyrimidin-4-yl}-N-cyclopropyl-1H-indole-4-carboxamide hydrochloride

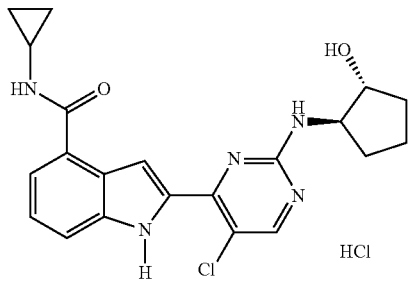 [SMILES: O=C(NC1CC1)c1cccc2[nH]c(-c3nc(N[C@@H]4CCC[C@H]4O)ncc3Cl)cc12 ; Cl]

A mixture of N-cyclopropyl-2-(2,5-dichloropyrimidin-4-yl)-1-(ethoxymethyl)-1H-indole-4-carboxamide (30 g, 75 mmol), (1R,2R)-2-aminocyclopentanol hydrochloride (12.3 g, 90 mmol) and DIPEA (37.5 mL, 225 mmol) in DMSO (150 mL) is stirred at 80° C. for 16 h, then poured into water (1 L), and extracted with EA (2×500 mL). The combined extracts are washed with aqueous saturated sodium chloride (500 mL), dried over Na$_2$SO$_4$ and concentrated in vacuo. The residue is purified by chromatography on silica gel to give 2-{5-chloro-2-[(1R,2R)-2-hydroxycyclopentylamino]pyrimidin-4-yl}-N-cyclopropyl-1-(ethoxymethyl)-1H-indole-4-carboxamide (33 g, 93%). MS (m/z): 470 ($^{35}$Cl) and 472 ($^{37}$Cl) (M+H)$^+$.

The above product (33 g, 70 mmol) is stirred with hydrogen chloride (6 M in methanol, 1 L, 6 mol) at 45° C. for 16 h. The precipitate is collected by filtration, washed with methanol (2×300 mL) and dried in vacuo to give the title compound (26.8 g, 85%). MS (m/z): 412 ($^{35}$Cl) and 414 ($^{37}$Cl) (M+H)$^+$.

Intra-articular administration of a dominant-negative IKKβ significantly reduced the severity of the adjuvant-induced arthritis in rats (Tak P P et al, *Arthritis Rheum.* (2001) 44(8)1897-1907). IKKβ knockout cells have dramatic defects in expressing TNFα-induced cytokines, chemokines, or adhesion molecules. Through conditional or tissue-specific knockout of IKKβ, this kinase is found to be required for survival and proliferation of peripheral B-cells and for prevention of apoptosis mediated by TNFα (Li Z-W, Omori A S, Labuda T, Karin M, Rickert R C, "IKKβ is required for peripheral B cell survival and proliferation" *The J. Immunol.*, (2003), 170:4630-4637; Maeda S, Chang L, et al. "*IKKβ is required for prevention of apoptosis mediated by cell-bound but not by circulating TNFα*" *Immunity*, (2003), 19:725-737). Moreover, deletion of IKKβ in myeloid cells also reduced the growth of colitis-associated cancer (Greten F R et al, Cell, (2004), 118:285-296,). Furthermore, several groups have demonstrated that IKKβ kinase inhibitors can induce cell growth inhibition and/or augment TNFα- or TRAIL-induced cell death in different cancer cell lines (Takaomi et al *Clinical Cancer Res.*, (2005), Vol 11:1974-82; Hideshima et al, *JBC*, (2002) 277:16639-47; Lam et al *Clinical Cancer Res.*, (2005) Vol 11:28-40).

Additionally WO07092095 discloses inhibitors of IKKβ useful in treating multiple myeloma, colon cancer, large cell lung cancer, glioblastoma, and ovarian cancer.

Assessments of the Biological Properties

The biological properties of a compound of the present invention can be determined by the following assays Inhibitory activity of IKKβ by a compound of the present invention is evaluated by an enzymatic IKKβ-kinase assay that measures the phosphorylation of IKBα substrate by the respective kinases, and by a cellular viability assay that measures the ability of the compounds to inhibit cell growth in a variety of tumor cell lines including BxPC-3 and Skov3-luc. The anti-tumor effects of a compound of the present invention are determined by both an IVTI (in vivo target inhibition) U87MG model that measures the effect of the compound on the inhibition of TNFα gene expression in U87MG Xenograft, and several Xenograft efficacy models including the effect of the compound alone on human ovarian cancer SKOV-3x-FF-luci tumor growth in nude mice, and the combination studies of testing the compound with either vincristine (VCR) in human ovarian cancer SKOV-3x-FF-luci Xenograft or CPT-11 in Human Colon Cancer HT-29 Xenograft. Anti-inflammatory activity of a compound of the present invention is determined by a Lipopolysaccharide (LPS) IVTI (in vivo target inhibition) model that assesses the ability of the compound to inhibit the LPS-induced plasma cytokine production in mouse.

Anti-inflammatory activity of a compound of the present invention is investigated in both IVTI (in vivo target inhibition) and IVEF (in vivo efficacy) models. Lipopolysaccharide (LPS) IVTI models in both mouse and rat are used to assess the ability of the compound to inhibit the LPS-induced production of plasma cytokine. Collagen Induced Arthritis (CIA) models in mouse and rat are used to evaluate the anti-inflammatory and anti-cytokine effects. Ovalbumin (OVA)-induced pulmonary inflammation models in mouse and rat are used to evaluate the effect of the compound on OVA-induced airway inflammation. Experimental autoimmune encephalomyelitis (EAE) model in mouse, an animal model for multiple sclerosis, and Dinitrobenzene Sulphonic Acid (DNBS)-induced Colitis model in rat are also used for the assessment of the anti-inflammatory and anti-cytokine effects.

These assays demonstrate that Example 1 and 2 are potent inhibitors of IKKβ and at least one of the compounds has anti-inflammatory or anti-cancer activity.

IKKβ Kinase Assay

The IKKβ kinase assay is used to assess the effect of a compound of the present invention on the enzymatic activity of IKKβ kinase. The IKKβ kinase assay is performed in vitro using an IKKβ-Inhibitor Screening Kit (Calbiochem., Cat.No. CBA044). All reactions (50 μL) are started by adding 10 μL of kinase buffer (kit component, No. JA9130), 10 μL of GST-IKBa substrate (IKKb substrate, kit component, No. JA9127), 10 μL of IKKβ (2.5 ng/well, kit component, No. 481404), 10 μL of the test compound (DMSO solution) or H$_2$O, and 10 μL of ATP/MgCl$_2$ (kit component, No. JA7914) and then incubating at 30° C. for 30 min. The contents of the wells are then discarded. Each well is washed 3 times with 200 μL 1× wash buffer (kit component, NO. JA1617, 1:20 dilution). 100 μL of anti-phospho IκBα (Ser$^{32}$/Ser$^{36}$) antibody conjugate (kit component, No. JA9126) is added to each well and incubated at room temperature for 1 h. Then the wells are washed 3 times with 1× wash buffer (kit component, NO. JA1617, 1:20 dilution), 200 mL/well and 100 μL HRP-conjugate (kit component, No. JA7643) is added to each well and incubated at room temperature for 1 h. Then the wells are washed 3 times with 200 μL 1× wash buffer (kit component, NO. JA1617, 1:20 dilution) and 100 μL TMB substrate conjugate (kit component, No. JA1608) is added to each well. The plate is incubated at room temperature until the color changes. 100 μL of ELISA Stop solution (kit component, NO. JA1616) is then added to each well. The data is collected at 450 nm with a reference wavelength at 570 nm by MultiScan (Thermo Labsystems). All compound are tested at 8 concentrations (10 μM to 0.003 μM) using a 1:3 serial dilution scheme. All exemplified compounds in the invention show an $IC_{50}$<0.1 μM. For example, Example 1 has an $IC_{50}$ of 0.015 μM, which indicates that the compound is a potent IKKβ inhibitor.

Alternately, the IKKβ kinase assay is performed in vitro using a Z'-LYTE™ Assay Kit-Ser/Thr 5 Peptide (Invitrogen, Cat.No. PV3178). All reactions (20 μL) are started by adding 0.8 μL of the test compound in a DMSO solution, 10 μL of Kinase/Peptide Mixture or Phospho-Peptide solution (Invitrogen, Cat.No. PV3219, diluted with 1.33× Kinase Buffer), 5 μL of 1.33× Kinase Buffer (Invitrogen, Cat.No. PV3189, 5× diluted with distilled water) or ATP Solution (5 μM), and 4.2 μL of distilled water. The 384-well assay plate (Corning, Cat.No. 3575) is mixed and incubated at room temperature for 1 hour. 10 μL of the Development Solution [Development Reagent B (Invitrogen, Cat.No. PV3296)/Development Buffer (Invitrogen, Cat.No. PV3127)=1:128] is then added to each well, mixed and incubated at room temperature for another 1 h. The kinase reaction is then stopped by adding 10 μL of the Stop Reagent (Invitrogen, Cat.No. PV3094), and the plate is read with a Wallac 1420 VICTOR$^3$ Multilabel Counter (PERKIN ELMER™) at 445 nm and 520 nm fluorescence. The assay has an MSR of 2.14. The compound is initially tested at 8 concentrations (10 μM) to 0.003 μM) using a 1:3 serial dilution scheme. Example 2 has an IC50 of 0.05811 μM. This result shows that Example 2 is also a potent IKKβ inhibitor.

Cell Viability Test

To evaluate biological activity of a compound in vitro, the cell viability test is applied, in which, IKKβ receptor plays an important role in cell survival and proliferation. Once the IKKβ pathway is blocked by inhibitors, a cell can go through apoptosis or death. The cell viability test provides information on cell survival after treatment with IKK inhibitors.

BxPC-3 cells (ATCC #CRL-1687; human pancreatic cancer cell line) are grown in Roswell Park Memorial Institute (RPMI) 1640 media (Gibco #A10491-01) supplemented with 10% fetal bovine serum (FBS) (Gibco #10099-141). Skov3-luc cells (ATCC, human ovarian carcinoma cell line) are grown in McCoy's 5a medium (Gibco#16600) supplemented with 10% FBS (Gibco#10099-141). For compound testing, BxPc-3 and Skov3-Luc cells are seeded at 2000 and 5000 cells/well respectively in 100 μL of corresponding media specified above for each cell line in 96-well plates 20 h prior to treatment. Cells are treated with a test compound at eight different concentrations in the presence of 0.5% DMSO for 72 h. Cell death in each well is determined by the addition of 20 μL of the One Solution Reagent (CELLTITER 96® AQueous One Solution Cell Proliferation Assay, Promega #G3580). After 2-4 h of incubation at 37° C., optical densities at 492 nm are measured with a microplate reader Inhibition of cell viability is determined by comparison to the control cells treated in the absence of a test compound.

For the combination study of the compound with other antitumor agents, BxPc-3 and Skov3-Luc cells are seeded at 2000 and 5000 cells/well respectively in 100 μL corresponding media specified above for each cell line in 96-well plates 20 h prior to the treatment. The cells are treated with the test compound at a number of concentrations for 30 minutes and then exposed to 5 ng/mL TNFα or 0.15-0.6 uM of VCR (vincristine sulfate) for an additional 72 hours. Cell death in each well is determined by the addition of 20 μL of the One Solution Reagent (CELLTITER 96® AQueous One Solution Cell Proliferation Assay, Promega #G3580). After 2-4 h of incubation at 37° C., optical densities at 492 nm are measured with a microplate reader Inhibition of cell viability is determined by comparison to the control cells treated in the absence of a test compound. For example, the results of the combination study with Example 1 are specially detailed in Table 2. Example 1 shows synergy effects (the effects of Example 1 are enhanced or magnified, see table 2-in Bxpc-3 cell line: Example 1 (2.5 uM) alone, −16.48% inhibition; TNFα (5 ng/mL) alone, 5.73% inh ; TNFα (5 ng/mL)+Example 1 (2.5 μM), 87.75% inhibition also in Bxpc-3 cell line, Example 1 (25 μM) alone, 11.5% inh.; Vincristine (0.15 μM) alone, 5.73% inhhibition; Vincristine (0.15 μM) +Example 1 (25 μM), 80.25% inhibition) when combined with either TNFα or VCR in inhibiting Bxpc-3 and Skov3 tumor cell growth. This data demonstrates the therapeutic utility of Example 1 in combination with TNFα or VCR in the treatment of ovarian cancer or pancreatic cancer.

TABLE 2

Combination use of Example 1 with other anticancer agents

| Cell line | Agents | Ave. Inhibition rate |
|---|---|---|
| Bxpc-3 | TNFα (5 ng/mL) | 5.73% |
|  | Example 1 (2.5 μM) | −16.48% |
|  | TNFα (5 ng/mL) + Example 1 (2.5 μM) | 87.75% |
| Bxpc-3 | Vincristine (0.15 μM) | 9.48% |
|  | Example 1 (25 μM) | 11.53% |
|  | Vincristine (0.15 μM) + Example 1 (25 μM) | 80.25% |
| Skov3-luc | Vincristine (0.25 μM) | 24.96% |
|  | Example 1 (12.5 μM) | 21.76% |
|  | Vincristine (0.25 μM) + Example 1 (12.5 μM) | 82.29% |

Inhibition of TNFα Gene Expression in U87MG Xenograft

TNFα stimulates IKKβ signaling and triggers TNFα gene expression. In order to confirm that a compound is targeting IKKβ in vivo, the compound is screened for its ability to inhibit TNFα induced TNFα gene expression in a U87MG (human glioblastoma cell line) xenograft. $3\times10^6$ U87MG tumor cells are implanted subcutaneously into the right lateral flank of female Balb/c athymic nude mice (6-8 weeks old). After 10-12 days, when tumor volume reached 200-300 mm$^3$, animals are randomized into the following groups: control (non-TNFα stimulation), model (TNFα stimulation), and the test compound treated groups: 10, 30, 60 and 100 mg/kg (with TNFα stimulation). Nude mice are orally administered with the test compound at 2 h prior to tumor harvesting. TNFα (R&D, Cat: 210-TA) is intravenously injected at 1 h before tumor harvesting at 8 μg/kg.

Total RNA is extracted using the RNEASY® mini Kit (QIAGEN®, Cat: 74126). cDNA is synthesized using the High Capacity cDNA reverse transcription kit (ABI, Cat: 4368813). Quantitative real-time PCR is carried out in a 7500 real-time PCR system (Applied Biosystems) using the corresponding primers/probes for human GAPDH gene(ABI Hs99999905_ml) and human TNFα gene(ABI Hs00174128_ml) and ABgene Absolute QPCR ROX 2× master mix(AB-1139/B).

TNFα gene expression is normalized to β-actin gene expression. The gene counts are read from PCR machine Inhibition (%)=(Counts of Model—Counts of Treatment)/(Counts of Model-Counts of Control)×100%. Example 1 is specifically detailed in Table 3. Example 1 dose-dependently inhibits the TNFα induced TNFα gene expression in U87MG xenograft.

TABLE 3

Effect of Example 1 on TNFα induced TNFα gene expression in U87MG xenograft model

| Groups | Inhibition Rate (%) |
|---|---|
| Control (without TNFα) | — |
| Model (with TNFα) | — |
| Example 1-10 mg/kg -2 h | 49.1 |
| Example 1-30 mg/kg-2 h | 68.5 |
| Example 1-60 mg/kg-2 h | 86.2 |
| Example 1-100 mg/kg-2 h | 94.9 |

Example 2 is specifically detailed in Table 4, Example 2 dose-dependently inhibits the TNFα induced TNFα gene expression in U87MG xenograft.

TABLE 4

Effect of Example 2 in TNFα induced TNFα gene expression in U87MG Xenograft Meodel.

| Groups | Inhibition Rate (%) |
|---|---|
| Control | — |
| Model | — |
| Example 2 - 3 mg/kg | 10.7 |
| Example 2 - 10 mg/kg | 25.3 |
| Example 2 - 30 mg/kg | 69.7 |
| Example 2 - 60 mg/kg | 87.8 |

Examples 1 and 2 show that the inhibition of TNFα induced TNFα gene expression in U87MG xenograft is in a dose-dependent manner.

Anti-tumor Effects in Human Ovarian Cancer SKOV-3x-FF-luci Xenograft SKOV-3x-FF-luci human ovarian cancer line cell line (ATCC) is cultured in McCoy's 5a medium containing 10% fetal calf serum (FCS). Female Balb/c nu/nu mice (6-8 weeks old) are peritoneally injected with 0.2 mL of cell suspension containing $2\times10^6$ cells. Mice are divided into five groups six days after cell implantation. The test compound at doses of 60, 90 and 150 mg/kg is orally administered to animals for a consecutive 21 days with a twice a day (bid) or three times a day (tid) regimen. Mice in control groups are administered the vehicle (10% Acacia at pH 2.1, bid). At the end of the treatment, all mice are euthanized with $CO_2$ and tumors in the peritoneal cavity, diaphragmatic muscle, mesenterium, liver, spleen, and ovaries are dissected and harvested, and put together for the measurement of their combined weight. Results of tumor weight and inhibition rate (IR) are evaluated. The inhibition rate is calculated with the formula: IR %=(tumor weight in control−tumor weight in drug treated)/tumor weight in control×100%. The results for Example 1 are specially detailed in Table 5. Example 1 significantly inhibits human ovarian tumor growth with an IR of 76.31% at oral doses of 60 mg/kg (t.i.d.) in nude mice (P<0.01, Student's T test). This data demonstrates the therapeutic utility of Example 1 in the treatment of ovarian cancer.

TABLE 5

Effects of Example 1 in SKOV-3x-FF-luci tumor growth in nude mice

| Group | Animal # (start/end) | Tumor Weight (g) (Mean ± S.D.) | IR | P Value vs control |
|---|---|---|---|---|
| Control (10% *Acacia* pH 2.1, bid, q8 h) | 8/8 | 2.148 ± 0.530 | — | — |
| Example 1 (60 mg/kg, tid, q6 h) | 8/8 | 0.509 ± 0.193 | 76.31% | 0.0001 |

Alternately, the test compound is evaluated for its anti-tumor effects on tumor growth of human ovarian cancer SKOV-3x-FF-luci in nude mice. SKOV-3x-FF-luci cell line (ATCC) is cultured in McCoy's 5a medium containing 10% fetal calf serum. Female Balb/c nu/nu mice (6-7 weeks old) are injected peritoneally with 0.2 mL of cell suspension containing $2\times10^6$ cells. Mice are randomized and divided into four groups six days after cell implantation. The test compound at doses of 30 and 100 mg/kg is orally administered to animals twice a day for 23 consecutive days. Mice in the control group are administered the vehicle (10% Acacia), twice a day. Mice in the positive control group are injected with Cisplatin (4 mg/kg) via the tail vein once a week. At the end of the treatment, all mice are euthanized with $CO_2$ and tumor nodules in the peritoneal cavity, diaphragmatic muscle, mesenterium, liver, spleen, and ovaries are dissected, harvested, and combined for the measurement of weight. Inhibition rate: IR %=(tumor weight in control−tumor weight in drug treated)/tumor weight in control×100%). Example 2 shows a tumor inhibition rate (IR) of 59.3% and 93.9% at doses of 30 and 100 mg/kg, respectively. By monotherapy, Example 2 also inhibits SKOV-3x-FF-luci tumor growth. This data demonstrates the therapeutic utility of Example 2 in the treatment of ovarian cancer.

Anti-tumor Effects in Human Colon Cancer HT-29 Xenograft

IKKβ inhibitor has been reported to repress the HT-29 tumor growth when in combination with CPT-11 (Lagadec P, Griessinger E, Nawrot M P, et al. Br. J. Cancer (2008) 98, 335-344). The anti-tumor effect of the compound is then examined in a human colon cancer HT-29 xenograft in combination with CPT-11. The compound is tested for its anti-tumor effects in a human colon cancer HT-29 xenograft with/without the co-administration of CPT-11 essentially as described in a method reported in the literature (Lagadec P, Griessinger E, Nawrot M P, et al. Br. J. Cancer (2008) 98, 335-344).

The HT-29 human colorectal adenocarcinoma cell line is obtained from ATCC and cultured in McCoy's 5a medium containing 10% fetal calf serum. Male Balb/c nu/nu mice (6-7 weeks old) are injected subcutaneously in the right lateral flank with 0.1 mL of cell suspension containing $3.0\times10^6$ cells. Mice are divided into six groups, seven days after cell implantation. The test compound is orally administered twice a day at 60 and 20 mg/kg. CPT-11 at 20 mg/kg is peritoneally administered twice a week. In combination treatment, CPT-11 is given 1 h after the administration of the test compound. Mice from the control group are orally administered the vehicle (10% Acacia at pH2.1), twice daily; and peritoneally dosed with saline, twice a week. Two orthogonal diameters of the tumor are measured with digital vernier calipers three times a week. Tumor volume (TV) is measured and recorded during treatment period by the formula: TV=Length×Width$^2$/

2. Tumor Growth Inhibition (TGI) for absolute tumor volume is calculated by the following equations where $V_0$ is the tumor volume at day 0 (grouping day) and $V_t$ is the tumor volume at measurement day t: TGI=$[1-(V_t-V_0)_{drug\ treated}/(V_t-V_0)_{vehicle\ control}]\times 100\%$. Mice are euthanized on the following conditions: 1) At the end of study (Day 66); 2) Individual TV>4000 mm$^3$; 3) Individual tumor ulcerated. Example 1 as a single agent does not inhibit HT-29 tumor growth at 60 or 20 mg/kg, p.o., but when in combination with CPT-11 (20 mg/kg, i.p.), it enhances the anti-tumor effect of CPT-11 at these dosages (P<0.05, Student's T test).

In combination with CPT-11, Example 1 shows anti-tumor effects in human colon cancer HT-29 Xenograft model, indicating Example 1 plays a role in the tumor repression. This data demonstrates the therapeutic utility of Example 1 in combination with CPT-11 in the treatment of colon cancer.

Antitumor Effect in SKOV-3x-FF-luci Xenograft with Vincristine (VCR)

In order to expand the anti-tumor spectrum, more combination testing is explored. Based on in vitro synergistic effect of Example 1 and VCR, the compound is tested for its anti-tumor effects in SKOV-3x-FF-luci xenograft in the presence/absence of VCR. The SKOV-3x-FF-luci human ovarian cancer line (ATCC) is cultured in McCoy's 5a medium containing 10% FCS. Female Balb/c nu/nu mice (6-7 weeks old) are peritoneally injected with 0.2 mL of cell suspension containing $2\times 10^6$ cells. Mice are divided into nine groups six days after cell implantation. The test compound is orally administered twice a day at 60 mg/kg for 20 consecutive days or at 90 mg/kg with a 2 days on and 5 days off dosing schedule. VCR at 1 or 0.3 mg/kg is administered via tail vein injection, once a week. In the combination group, VCR is given 1 h after the administration of the test compound. Mice from the control group are administered with the oral vehicle (10% Acacia at pH2.1) and intraperitoneally injected with saline. At the end of the treatment, all mice are euthanized with $CO_2$ and tumors in the peritoneal cavity, diaphragmatic muscle, mesenterium, liver, spleen, and ovaries are harvested with surgery scissors and weighted. At suboptimal dose, VCR inhibits the tumor growth by 38%; Example 1 inhibits the tumor growth by 42% and 36% at 60 mg/kg and 90 mg/kg, respectively. In the combination group, tumor growth is inhibited by 76% and 74%. Compared with monotherapy, statistical significance is found between combination and monotherapy. Therefore, Example 1 demonstrates synergistic effect when combined with VCR, suggesting that Example 1 has relative wide anti-tumor spectrum when combining with different chemotherapy agents. This data also specifically demonstrates the therapeutic utility of Example 1 in combination with VCR in the treatment of ovarian cancer.

Lipopolysaccharide (LPS)-Induced Plasma Mouse Cytokine Production Model

To evaluate the compound's inhibitory effect on inflammation in vivo, the compound is screened for its ability to inhibit LPS-induced plasma cytokine production.

Balb/c mice (female, body weight from 18 to 20 g) are used in these experiments. The dose dependency, time course study and pharmacokinetic/pharmacodynamic relationship of the test compound are conducted in mice treated with LPS (0.4 mg/kg).

Eight mice/group are administrated with 1 to 100 mg/kg of either the test compound (suspension in 10% acacia) or vehicle by oral gavage at 1 h prior to intraperitoneal injection of 0.4 mg/kg LPS. Ninety minutes after LPS administration, blood samples are collected in tubes containing heparin for anticoagulation. Plasma samples are diluted 3-fold with dilution buffer (R&D, Cat.No. Part 895206, Calibrator Diluent RD5Z). TNFα levels are measured using ELISA kit (R&D, Cat.No. MTA00) based on manufacture's protocol. Data is acquired using a SPECTRAMAX® M2e Plus Plate Reader and analyzed by standard curve fitting. Example 1 at 10 mg/kg significantly suppresses the production of TNFα down to 1474.9 pg/mL from a baseline of 2346.2 pg/mL (p<0.01), an inhibition of 37.1%.

Alternately, the compound is screened for its ability to inhibit the LPS-induced cytokine production in rat plasma according to the method reported in the literature (Ziegelbauer K, Gantner F, Lukacs N W, et al. Br J. Pharmacol. 2005,145(2):178-92). Briefly, Lewis rats (male, body weight 140 g-180 g) are used in the experiments. Animals (8/group) are given 1 to 100 mg/kg of the testing compound (suspension in 35% solutol & 60% PEG400 & 5% PG) or vehicle by oral gavage at 1 h prior to intraperitoneal administration of LPS 0.4 mg/kg. Ninety minutes after the intraperitoneal administration of LPS, blood is collected in heparin anticoagulated tubes to measure TNFα using R&D System ELISA Kit based on the general Kit protocols. The plasma sample is diluted 100 fold with the dilution buffer and 50 μL of diluted sample is used in each measurement. The plate is read on a SPECTRAMAX® M2e Plus Plate Reader and TNFα levels are analyzed based on the standard curve. The drug levels in plasma are measured with LC-MS-MS. Example 2 dose dependently inhibits plasma TNFα production with an $ED_{50}$ value of 19.8±10.9 mg/kg and an $EC_{50}$ value of 4.042±1.28 μg/mL. Alternately, the compound is screened for its ability to inhibit the LPS-induced cytokine production in mouse plasma. Balb/c mice (female, body weight 18-20 g) are used in the experiments. Mice (8/group) are administrated with 1 to 100 mg/kg of the test compound (suspension in 10% acacia) or vehicle by oral gavage at 1 h prior to introperitoneal (i.p.) administration of LPS (0.4 mg/kg). Ninety minutes after LPS administration, blood is collected with heparin anticoagulated tubes to measure TNFα levels (R&D, Cat.No. MTA00), IL-6 (R&D, Cat.No. M6000B) and IL-1β (R&D, Cat.No. MLB00B) based on the general kit protocols. Diluted or undiluted plasma samples of 50 μL are used for each measurement. For the measurements of TNFα, the plasma sample is diluted 3-fold with the dilution buffer (R&D, Cat.No. Part 895206, Calibrator Diluent RD5Z); for the measurements of IL-6, the plasma sample is diluted 25 fold with the dilution buffer (R&D, Cat.No. Part 895175, Calibrator Diluent RD5T) and undiluted plasma sample is used for the measurement of IL-1β. The plate is read on a SPECTRMAX® M2e Plus Plate Reader and the data is analyzed using a standard curve. Example 2 dose dependently inhibits TNFα and IL-6 production in plasma with an $ED_{50}$ of 4.84 mg/kg ($EC_{50}$ in the 2420 ng/mL range) and 15.1 mg/kg, respectively, but no effect was observed on IL-1β production even at the dose of 100 mg/kg.

Both Example 1 and 2 are confirmed to be potent IKKβ inhibitors in vitro and show significant activity in a mouse model of LPS-induced cytokine release in vivo.

LPS-Induced Acute Joint Inflammation in Rat

Intra-articular administration of a dominant-negative IKKβ significantly reduced the severity of adjuvant-induced arthritis in rats (Tak P P et al, *Arthritis Rheum.* (2001) 44(8) 1897-1907). To further investigate the effects of IKKβ inhibitor on mechanism-relevant joint inflammation, the compound is screened for its ability to inhibit the LPS-induced joint acute inflammation in rat essentially as describe by a method reported in the literature (Matsukawa A, Yoshimura T, Miyamoto K, Ohkawara S, Yoshinaga M. Lab Invest. 1997, 76(5): 629-38). Briefly, Wistar rats (female, body weight 150 g-170 g) are used in the experiments Animals (8/group) are given 1 to 100 mg/kg of the test compound [suspension in 35% Solutol (Macrogol 15 Hydroxystearate) & 60% PEG400 & 5% PG (propylene glycol)] or vehicle by oral gavage at 1 h prior to intra-articular (i.a.) administration of 10 µg of LPS in 10 µL of saline on left hind knee of each rat, using a 26-gauge needle. The right hind knee of each rat is injected with 10 µL of saline as a control. Two hour after LPS injection, each ankle of the rats is lavaged with 100 µL of saline. The synovial fluids are collected and stored at -80° C. The plasma is diluted 2 fold with the dilution buffer and 50 µL of the diluted sample is used for the measurement of TNFα levels using R&D System ELISA Kit based on the general Kit protocol. The plate is read on a SPECTRAMAX® M2e Plus Plate Reader and TNFα levels are analyzed using a standard curve. The drug levels are also measured by liquid chromatography-tandem mass spectrometry (LC-MS-MS). Example 2 dose dependently inhibits joint TNFα production with an $ED_{50}$ 23.4 mg/kg. The data also shows that the inhibition of TNFα production correlates with drug plasma concentrations and joint concentration. Collectively these data indicate that the compound of Example 2 inhibits joint inflammation.

Protocol of Collagen Induced Arthritis (CIA) Model in Mice

Previous studies have shown that small molecular inhibitors of IKKβ are efficacious in a mouse CIA model (Podolin, P L et al, J. Pharm. Exp. Ther., 2005, 312: 373-381). In addition, mice with T cells expressing a dominant—negative form of IkBa are protected from developing CIA (Seetharaman R. et al. J. Immunol. 1999: 163, 1577-1583). These observations suggest that IKKβ inhibitors are likely to be efficacious in treating rheumatoid arthritis. Therefore a compound of the present invention is tested in the collagen induced arthritis (CIA) model in mice essentially as described in a method reported in the literature (Rosloniec E F, Cremer M, Kang A, Myers L K. Current Protocols in Immunology. 1996, 15.5.1-15.5.24).

Briefly, DBA/1 mice are immunized intradermally with chicken collagen II (200 µg/mouse) emulsified with Freund's complete adjuvant (CFA, Sigma, US) on day 0 and day 21 to elicit arthritis. The severity of arthritis is assessed using a visual scoring system, in which each paw is graded from 0 to 4 (0=normal, 4=severe swelling of the entire paw). The hind joint thicknesses are measured with a micrometer. The testing compound is orally administered for either prophylactic or therapeutic purposes. For the prophylactic study, the testing compound is orally administered twice daily from day 1 to day 42. For the therapeutic study, the drug treatment is started after the onset of arthritis, which usually occurs within one week of 2nd immunization. Mice are treated with the drug for 21 days.

Lefunomide (LEF), an immunosuppressive agent, is used at 10 mg/kg/day once-daily (q.d.) as a positive control. Normal animals, not receiving any treatment, are used as negative control. The drugs are orally administered at 3, 10, and 30 mg/kg bid for 42 days. Statistically significant inhibition of joint swelling and reduction of arthritis scores are observed at 10 and 30 mg/kg bid (20 and 60 mg/kg/day) for Example 2 with an $ED_{50}$ of 4.3 mg/kg.

This data demonstrates the therapeutic utility of Example 2 in the treatment of rheumatoid arthritis.

Rat Collagen II Induced Arthritis (CIA) Model

To confirm the results obtained in mouse CIA model, the compound is also tested in a CIA model in rat essentially as described in a method reported in the literature (Rosloniec E F, Cremer M, Kang A, Myers L K. Current Protocols in Immunology. 1996, 15.5.1-15.5.24). Briefly, Wistar Rats are immunized intradermally with 200 µg bovine collagen II emulsified in Freund's incomplete adjuvant (IFA, Sigma, US) on day 0 and with 100 µg collagen II emulsified in IFA (incomplete Freund's adjuvant) on day 7. The hind paw volume is measured before and after the immunization. The disease development of four paws is quantified with arthritis scores. Rats in normal and model groups are treated with vehicle or drug (treated group). Rats in treated group are orally administered with the testing compound at doses of 3, 10, 30 mg/kg (bid), from day 1 to day 21 after the first immunization. In the LEF group, as a positive control, rats are orally administered with LEF at a dose of 10 mg/kg, q.d. Example 2 at 30 mg/kg significantly attenuates collagen induced arthritis, as shown by decreased arthritis scores and hind paws volume. This data demonstrates the therapeutic utility of Example 2 in the treatment of rheumatoid arthritis.

Ovalbumin (OVA)-induced Pulmonary Inflammation in Mice

Previous studies have shown that small molecular inhibitors of IKKβ can suppress allergen-induced airway inflammation and hyper-reactivity in mice (Birrell M A etal, Am J Respir Crit Care Med, 2005, 172: 962-971). The purpose of this study is to investigate the effects of IKKβ inhibitors on an in vivo model of antigen-driven airway inflammation.

A compound of the present invention is tested in an OVA-induced pulmonary inflammation model in mice essentially as described in a method reported in the literature (Muriel Pichavant, Sho Goya, Eckard Hamelmann, Erwin W. Gelfand, and Dale T. Umetsu. Animal Models of Airway Sensitization. Current Protocols in Immunology. (1999) 15.18.1-15.18.13). Briefly, female Balb/c mice weighing from 18 to 20 g are sensitized by introperitoneal injection of 100 µL of saline containing 20 µg of OVA and 2 mg of aluminum hydroxide on day 1 and 14. On days 28, 29 and 30, mice are challenged once each by aerosolizing 1% ovalbumin (OVA) in phosphate buffered saline (PBS) for 20 minutes with Buxco Mass Dosing System. Dexamethasone at the dose of 1 mg/kg (qd), serving as the positive control, and the test compound at doses of 1, 3, 10 and 30 mg/kg (qd) are orally administered to mice from day 1 to day 31. On day 32, animals from each group are anesthetized with 1% of pentobarbital sodium. The thoracic and abdominal cavities are opened and plasma is collected from centrifuged specimens. The trachea is then dissected and transected. Through the insertion of an 18-gauge catheter into the trachea, the lungs are lavaged with a total of 1.5 mL of sterile PBS and then placed into a specimen container. Cell-free BAL supernatants are obtained by centrifugation of BAL fluids. All serum and BAL supernatants are stored at −80° C. until use. Differential cell counts are performed on cytospin preparations of BAL cells for cell counting and cytokine determination. After the collection of BAL supernatants, the lungs of recipient mice are removed en bloc and fixed by an intratracheal instillation of 10% buffered formalin (in PBS). Three to six paraffin sections are obtained from the perihilar regions of recipient lungs, stained with hematoxylin and eosin, and examined under light microscopy for pathological study.

Compared with the normal control, OVA significantly increases eosinophils (p<0.01) and IL-13 (p<0.05) levels in the BALF. Dexamethasone at the dose of 1 mg/kg (qd), which serves as positive control, completely inhibits the increase of eosinophil cell numbers and decreases IL-13 by 77%. Example 2 at doses of 1, 3, 10, and 30 mg/kg (bid) decreases the eosinophil cell numbers by 58.6%, 49.3%, 94.1% (p<0.05) and 90.2% (p<0.05) respectively. Example 2 at doses of 10 and 30 mg/kg also significantly reduces IL-13 production by 73.0% (p<0.05) and 85.1% (p<0.01). In addition, hematoxylin and eosin stains show an improvement in pulmonary inflammation in mice treated with Example 2 at doses of 1 to 30 mg/kg group and dexamethasone at 1 mg/kg.

This study further demonstrates the therapeutic utility of Example 2 in the treatment of asthma.

OVA-induced Pulmonary Inflammation in Brown-Norway (BN) Rats

To evaluate the effects of IKKβ inhibitors on antigen-driven airway inflammation in vivo, the compound is also tested in OVA-induced pulmonary inflammation model in rats essentially as described in a method reported in the literature (Yamamoto N, Takeshita K, Shichijo M, Kokubo T, Sato M, Nakashima K, Ishimori M, Nagai H, Li Y F, Yura T, Bacon K B. J Pharm. Exp Ther. 2003; 306(3):1174-81). Briefly, male BN rats weighing from 240 to 260 g are sensitized by intraperitoneal injection of 1 mL of saline containing 1 mg of OVA and 13 mg of aluminum hydroxide on days 1, 2 and 3. Rats serving as normal control received 1 mL of saline instead of OVA. The test compound at doses of 0.3, 1, 3 and 30 mg/kg (bid) is orally administered to rats on day 20 and 21. On day 21 rats are challenged with 1% OVA for 15 minutes with Buxco Mass Dosing System. On day 22, rats are anesthetized with 1% Pentobarbital Sodium. The thoracic and abdominal cavities are opened. Plasma is collected from centrifuged specimens. The trachea is dissected and transected. Through the insertion of an 18-gauge catheter into the trachea, the lungs are lavaged with a total of 15 mL of sterile PBS, and then placed into a specimen container. Cell-free BAL supernatants are obtained by centrifugation of BAL fluids. All serum and BAL supernatants are stored at −80° C. until use. Differential cell counts are performed on cytospin preparations of BAL cells for cell counting and cytokine determination. OVA significantly increases the total cell numbers and eosinophile numbers in the BAL fluids compared with a normal control (p<0.01). Example 2 at 0.3 to 30 mg/kg significantly inhibits the increase of total cells and eosinophiles in a dose dependent manner (p<0.05), with an $ED_{50}$ at 0.49 mg/kg. This study further demonstrates the therapeutic utility of Example 2 in the treatment of asthma.

Mouse Experimental Autoimmune Encephalomyelitis (EAE) Model

CNS-restricted ablation of NEMO or IKK2 (IKKβ) but not IKK1 ameliorated disease pathology in a mouse model of multiple sclerosis (Nature Immunology, 2006; 7(9), 954-61). These studies suggest that IKKβ inhibitors should be efficacious in a mouse EAE model.

A compound of the present invention is tested in a PLP-139-151 induced EAE model in mice essentially as described in a method reported in the literature (Miller S D, Karpus W. I. Experimental autoimmune encephalomyelitis in the mouse. Current Protocols in Immunology. 1996, 15.1.1-15.1.13). Briefly, female SJL/J mice are immunized intradermally with PLP 139-151 (200 µg/mouse) emulsified with H37Ra (Mycobacterium tuberculosis strain) in CFA (Complete Freund's Adjuvant) (300 µg H37Ra). The test compound at doses of 3, 10, 30 mg/kg or vehicle is administered orally twice daily from day 1 after the immunization for the prophylactic study, or dosed from the day of EAE relapse and continues throughout the disease for the therapeutic study. Dexamethasone (1 mg/kg, p.o., q.d.) is used as the positive control. Body weight and clinical assessments of EAE are performed daily. Disease scoring follows the criteria: 0, no overt signs of disease; 1, limp tail or hind limb weakness but not both; 2, limp tail and hind limb weakness; 3, partial hind limb paralysis; 4, complete hind limb paralysis; 5, moribund state or death. Mice immunized with PLP 139-151 develop EAE-associated clinical symptoms and a decreased in body weight starting from day 11. EAE scores are rapidly elevated and reached a maximal level on day 15. A decrease of EAE scores occurs at approximately day 20. Then spontaneous relapse occurs thereafter (model group). In the drug groups with Example 2, the elevated EAE-associated clinical score decreases in a dose-dependent manner. The body weight loss improves with Example 2 at doses of 10 and 30 mg/kg. Example 2 at doses of 3, 10, and 30 mg/kg reduces the EAE clinical score, with an $ED_{50}$ of 3.7 mg/kg. This study demonstrates the therapeutic utility of Example 2 in the treatment of multiple sclerosis.

Dinitrobenzene Sulphonic Acid (DNBS)-Induced Colitis in Rat

IKKβ kinase is involved in the regulation of the expression of various pro-inflammatory proteins critical to the pathogenesis of inflammatory bowel diseases (IBD). Therefore IKKβ kinase represents a promising target for the development of novel agents to treat IBD.

A compound is tested in DNBS-induced colitis model in rat essentially as described in a method reported in the literature (Gut. 2002; 50(3):440-1). Briefly, Wistar rats are used in the experiments. Following the induction of distal colitis by intra-colonic instillation of DNBS, the test compound at doses of 3, 10, 30, 60 mg/kg (bid) is administered to rats orally for six days. The negative control group is treated with the vehicle alone without DNBS instillation. The vehicle-control group rats are DNBS-induced and treated with vehicle. In the positive control group, sulfasalazine is orally administered to the rats at 300 mg/kg daily for six consecutive days. Animals are euthanized 24 h after the final treatment. Colon-to-body weight ratio and colonic damage scores are calculated for each animal. Vehicle treatment of rats results in a progressive worsening of clinical symptoms, achieving a maximum colonic damage score of 6.1±0.6 and colon-to-body weight ratio-colon length of 0.96±0.10 on day 7 after instillation. In this DNBS-induced inflammatory bowel disease model, rats treated with Example 2 at doses of 3, 10, 30 and 60 mg/kg show a marked reduction in colonic damage scores, colon-to-body weight-to-colon length ratio with more than 30% reduction. The effects of Example 2 at 3 to 60 mg/kg/day are similar with that of sulfasalazine at 300 mg/kg/day.

This study demonstrates the therapeutic utility of Example 2 in the treatment of inflammatory bowel disease.

The compounds of the present invention are preferably formulated as pharmaceutical compositions administered by a variety of routes. Most preferably, such compositions are for oral or intravenous administration. Such pharmaceutical compositions and processes for preparing same are well known in the art. See, e.g., REMINGTON: THE SCIENCE AND PRACTICE OF PHARMACY (D. Troy, et al., eds., 21st ed., Lippincott Williams & Wilkins, 2005).

The compounds of the present invention are generally effective over a wide dosage range. For example, dosages per day normally fall within the range of about 0.05 to about 500 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. Compounds of the formula:

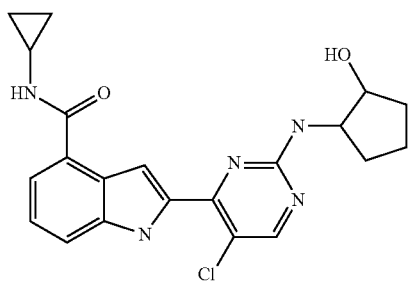 [SMILES: O=C(NC1CC1)c1cccc2[nH]c(-c3nc(NC4CCCC4O)ncc3Cl)cc12]

or a pharmaceutically acceptable salt thereof.

2. A compound or salt of claim 1 which is 2-{5-Chloro-2-[(1R,2R)-2-hydroxycyclopentylamino]pyrimidin-4-yl}-N-cyclopropyl-1H-indole-4-carboxamide.

3. A compound or salt of claim 1 which is 2-{5-Chloro-2-[(1R,2S)-2-hydroxycyclopentylamino ]pyrimidin-4-yl}-N-cyclopropyl-1H-indole-4-carboxamide.

4. A pharmaceutical composition comprising a compound or salt as in claim 1, in combination with one or more pharmaceutically acceptable carriers, diluents or excipients.

5. The pharmaceutical composition of claim 4 further comprising one or more other therapeutic agents.

6. The pharmaceutical composition of claim 5 wherein the therapeutic agent is TNFα.

7. The pharmaceutical composition of claim 5 wherein the therapeutic agent is vincristine.

8. A method of treating inflammatory diseases selected from the group consisting of rheumatoid arthritis, chronic obstructive pulmonary disease, asthma, multiple sclerosis, and inflammatory bowel disease, in a mammal comprising administering to a mammal in need of such treatment an effective amount of a compound or salt as in claim 1.

9. The method of claim 8 wherein the inflammatory disease is rheumatoid arthritis.

10. The method of claim 8 wherein the inflammatory disease is chronic obstructive pulmonary disease.

11. The method of claim 8 wherein the inflammatory disease is asthma.

12. The method of claim 8 wherein the inflammatory disease is multiple sclerosis.

13. The method of claim 8 wherein the inflammatory disease is inflammatory bowel disease.

14. A method of treating cancer selected from the group consisting of multiple myeloma, colon cancer, large cell lung cancer, glioblastoma, pancreatic cancer, and ovarian cancer, in a mammal comprising administering to a mammal in need of such treatment an effective amount of a compound or salt as in claim 1.

15. The method of claim 14 wherein the cancer is multiple myeloma.

16. The method of claim 14 wherein the cancer is colon cancer.

17. The method of claim 14 wherein the cancer is large cell lung cancer.

18. The method of claim 14 wherein the cancer is glioblastoma.

19. The method of claim 14 wherein the cancer is pancreatic cancer.

20. The method of claim 14 wherein the cancer is ovarian cancer.

21. A compound or salt as in claim 1 for use in therapy.

22. A compound or salt of as in claim 1 for the use in the treatment of inflammatory diseases.

23. The compound or salt for use according to claim 22 wherein the inflammatory disease is rheumatoid arthritis.

24. The compound or salt for use according to claim 22 wherein the inflammatory disease is chronic obstructive pulmonary disease.

25. The compound or salt for use according to claim 22 wherein the inflammatory disease is asthma.

26. The compound or salt for use according to claim 22 wherein the inflammatory disease is multiple sclerosis.

27. The compound or salt for use according to claim 22 wherein the inflammatory disease is inflammatory bowel disease.

28. A compound or salt as in any of claim 1 for the treatment of cancer.

29. The compound or salt for use according to claim 28 wherein the cancer is multiple myeloma.

30. The compound or salt for use according to claim 28 wherein the cancer is colon cancer.

31. The compound or salt for use according to claim 28 wherein the cancer is large cell lung cancer.

32. The compound or salt for use according to claim 28 wherein the cancer is glioblastoma.

33. The compound or salt for use according to claim 28 wherein the cancer is pancreatic cancer.

34. The compound or salt for use according to claim 28 wherein the cancer is ovarian cancer.

* * * * *